United States Patent
Nagasaki et al.

(10) Patent No.: US 9,621,839 B2
(45) Date of Patent: Apr. 11, 2017

(54) PROCESSING SYSTEM, MONITORING METHOD, AND NON-TRANSITORY COMPUTER-READABLE RECORDING MEDIUM

(71) Applicant: KABUSHIKI KAISHA YASKAWA DENKI, Kitakyushu-shi (JP)

(72) Inventors: Takashi Nagasaki, Kitakyushu (JP); Takashi Suyama, Kitakyushu (JP); Hirokazu Kariyazaki, Kitakyushu (JP)

(73) Assignee: KABUSHIKI KAISHA YASKAWA DENKI, Kitakyushu-Shi (JP)

( * ) Notice: Subject to any disclaimer, the term of this patent is extended or adjusted under 35 U.S.C. 154(b) by 0 days.

(21) Appl. No.: 15/012,869

(22) Filed: Feb. 2, 2016

(65) Prior Publication Data
US 2016/0227158 A1 Aug. 4, 2016

(30) Foreign Application Priority Data
Feb. 3, 2015 (JP) .................................. 2015-019792

(51) Int. Cl.

| | |
|---|---|
| *G11B 27/00* | (2006.01) |
| *H04N 5/93* | (2006.01) |
| *H04N 5/77* | (2006.01) |
| *G06F 19/00* | (2011.01) |
| *G06Q 10/06* | (2012.01) |
| *G05B 15/00* | (2006.01) |
| *G06F 7/00* | (2006.01) |
| *G05B 19/00* | (2006.01) |

(52) U.S. Cl.
CPC ............. *H04N 5/77* (2013.01); *G06F 19/366* (2013.01); *G06Q 10/06* (2013.01); *H04N 5/93* (2013.01); *Y10S 901/02* (2013.01)

(58) Field of Classification Search
CPC .......... G11B 27/00; H04N 5/93; G05B 15/00; G05B 19/00; G06F 7/00
USPC ...... 700/234, 1, 260, 261; 386/281, 278, 282
See application file for complete search history.

(56) References Cited

U.S. PATENT DOCUMENTS

| | | | | |
|---|---|---|---|---|
| 9,050,723 | B1* | 6/2015 | Elazary | G06F 11/0793 |
| 9,069,348 | B2* | 6/2015 | Kubota | G05B 19/409 |
| 2005/0256611 | A1* | 11/2005 | Pretlove | B25J 9/1664 |
| | | | | 700/264 |
| 2006/0293787 | A1* | 12/2006 | Kanda | G06N 3/008 |
| | | | | 700/245 |

(Continued)

*Primary Examiner* — Daquan Zhao
(74) *Attorney, Agent, or Firm* — Mori & Ward, LLP

(57) ABSTRACT

A processing system at least including a processing apparatus including a robot configured to perform, in accordance with operation commands, processes on a container that contains an object to be processed in a biochemistry, biotechnology, or life science field includes an image capturing apparatus and a monitoring apparatus. The image capturing apparatus continuously captures a moving image of the processes. The monitoring apparatus includes a storage unit, a list display unit, and a playback unit. The storage unit stores the moving image captured by the image capturing apparatus. The list display unit displays at least one of a list of the processes and a list of operation information items of each indicating an operation the robot. The playback unit plays the moving image from a timing corresponding to a process specified from the list of processes or an operation information item specified from the list of operation information items.

12 Claims, 11 Drawing Sheets

(56) References Cited

U.S. PATENT DOCUMENTS

| | | | |
|---|---|---|---|
| 2007/0260356 A1* | 11/2007 | Kock | B25J 9/1641 |
| | | | 700/261 |
| 2013/0067328 A1* | 3/2013 | Salyards | G06F 17/30769 |
| | | | 715/716 |
| 2013/0136417 A1* | 5/2013 | Kato | G11B 27/034 |
| | | | 386/241 |
| 2014/0285482 A1* | 9/2014 | Kim | G06T 13/40 |
| | | | 345/419 |
| 2016/0227158 A1* | 8/2016 | Nagasaki | H04N 5/77 |
| 2016/0311112 A1* | 10/2016 | Gustafsson | B25J 9/1656 |

* cited by examiner

PROCESSING SYSTEM, MONITORING METHOD, AND NON-TRANSITORY COMPUTER-READABLE RECORDING MEDIUM

CROSS-REFERENCE TO RELATED APPLICATIONS

The present disclosure contains subject matter related to that disclosed in Japanese Priority Patent Application JP 2015-019792 filed in the Japan Patent Office on Feb. 3, 2015, the entire contents of which are hereby incorporated by reference.

BACKGROUND

1. Field of the Invention

The present disclosure relates to a processing system, a monitoring method, and a non-transitory computer-readable recording medium.

2. Description of the Related Art

Operation procedures and conditions of a series of operations (hereinafter, collectively referred to as an "experiment") performed on an object, such as examination, cultivation, and amplification in a field such as biochemistry, biotechnology, or life science, are commonly called a protocol. Conducting an experiment based on a protocol is important to obtain a reproducible result or to verify the result of the experiment.

SUMMARY

According to an aspect of the disclosure, there is provided a processing system at least including a processing apparatus including a robot configured to perform, in accordance with operation commands, processes on a container that contains an object to be processed in a biochemistry, biotechnology, or life science field. The processing system includes an image capturing apparatus and a monitoring apparatus. The image capturing apparatus continuously captures a moving image of the processes. The monitoring apparatus includes a storage unit, a list display unit, and a playback unit. The storage unit stores the moving image captured by the image capturing apparatus. The list display unit displays at least one of a list of the processes and a list of operation information items each indicating an operation of the robot. The playback unit plays the moving image from a timing corresponding to a process specified from the list of processes or an operation information item specified from the list of operation information items.

According to another aspect of the disclosure, there is provided a method for monitoring a processing apparatus including a robot configured to perform, in accordance with operation commands, processes on a container that contains an object to be processed in a biochemistry, biotechnology, or life science field. The method includes continuously capturing a moving image of the processes, storing the captured moving image, displaying at least one of a list of the processes and a list of operation information items each indicating an operation of the robot, and playing the moving image from a timing corresponding to a process specified from the list of processes or an operation information item specified from the list of operation information items.

According to still another aspect of the disclosure, there is provided a non-transitory computer-readable recording medium storing a computer program that causes a computer to perform a process of monitoring a processing apparatus including a robot configured to perform, in accordance with operation commands, processes on a container that contains an object to be processed in a biochemistry, biotechnology, or life science field. The process for monitoring includes continuously capturing a moving image of the processes, storing the captured moving image, displaying at least one of a list of the processes and a list of operation information items each indicating an operation of the robot, and playing the moving image from a timing corresponding to a process specified from the list of processes or an operation information item specified from the list of operation information items.

According to yet another aspect of the disclosure, there is provided a processing system including a processing apparatus, an image capturing apparatus, and a monitoring apparatus. The processing apparatus includes a robot configured to perform, in accordance with operation commands, processes on a container that contains an object to be processed. The image capturing apparatus continuously captures a moving image of the processes. The monitoring apparatus includes a storage unit, a list display unit, and a playback unit. The storage unit stores the moving image captured by the image capturing apparatus. The list display unit displays at least one of a list of the processes and a list of operation information items each indicating an operation of the robot. The playback unit plays the moving image from a timing corresponding to a process specified from the list of processes or an operation information item specified from the list of operation information items.

DESCRIPTION OF THE EMBODIMENTS

According to the knowledge of the inventors of this disclosure, experiments greatly depend on an experimenter's skill in a field, such as biochemistry, biotechnology, or life science. For this reason, it is difficult to determine whether the obtained result is due to the experimenter's skill or due to other factors, and such a difficulty hinders objective verification. Accordingly, the inventors have studied removal of human-related factors by the use of a processing system including a robot to conduct an experiment.

Conducting an experiment with a robot makes the experiment more reproducible and consequently makes the result of the experiment more reliable. Further, recording the entire process of the experiment is thought to be desirable for cause analysis or reliability assurance of the obtained result. Specifically, to analyze an event that has occurred during the experiment in detail at a later time point or to prove that the processing system including a robot has been correctly operating at a later time point, it is desirable to record not only the result of the experiment but also the process of the experiment in a verifiable and analyzable manner.

The inventors have worked on the research and development to record the process of an experiment that is conducted based on a protocol by a processing system including a robot and have conceived a novel and creative idea related to a processing system, for example. Such a processing system, for example, will be described below with reference to an embodiment.

Figure 1:
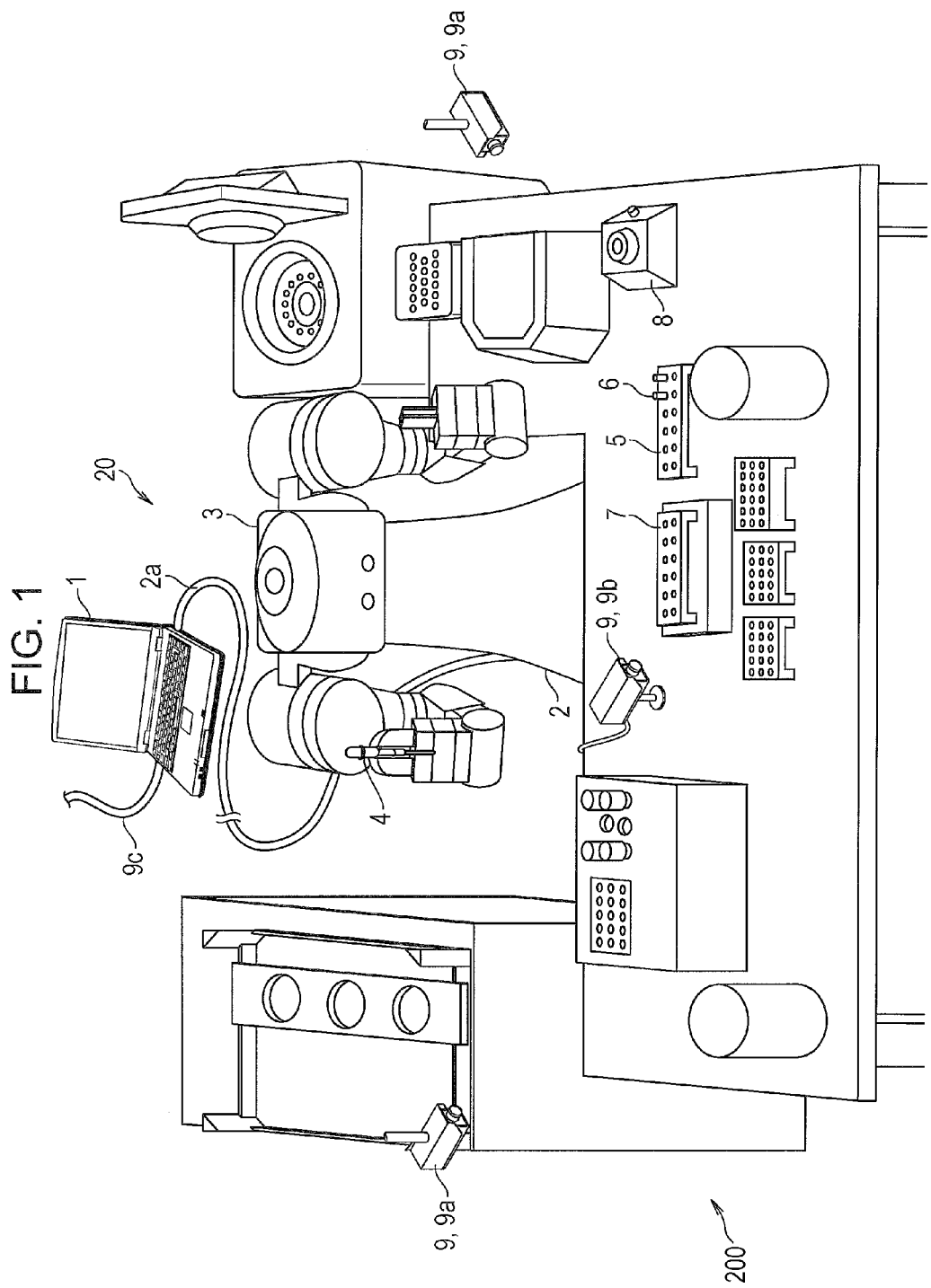
FIG. 1 is a schematic diagram illustrating a physical configuration of a processing system according to an embodiment of the disclosure.

FIG. 1 is a schematic diagram illustrating a physical configuration of a processing system 200 according to an embodiment of the disclosure. The processing system 200 includes a monitoring apparatus and protocol chart monitor apparatus (hereinafter, simply referred to as a "monitoring/monitor apparatus") 1, a robot controlling apparatus 2, an image capturing apparatus 9, and a processing apparatus 20. The processing apparatus 20 includes a robot 3 and peripheral devices for use in an experiment. The robot controlling apparatus 2 controls the robot 3 in accordance with operation commands generated based on a protocol chart. The robot 3 is controlled by the robot controlling apparatus 2 and conducts an experiment. The monitoring/monitor apparatus 1 is an apparatus in which a monitoring apparatus 1*j* (FIG. 3) and a protocol chart monitor apparatus 1*k* (FIG. 3) are integrated. The monitoring apparatus 1*j* monitors a series of processes performed during an experiment. The protocol chart monitor apparatus 1*k* displays a protocol chart, which visually illustrates a protocol being carried out. The monitoring/monitor apparatus 1 may be a dedicated device. However, the monitoring/monitor apparatus 1 is implemented by an ordinary computer herein. Specifically, a computer program that causes a commercially available computer to operate as the monitoring apparatus 1*j* and a computer program that causes the computer to operate as the protocol chart monitor apparatus 1*k* are executed on the computer, whereby the computer is used as the monitoring/monitor apparatus 1. These computer programs are provided typically as application software and are installed on a computer for use. The application software may be provided after being recorded on a Compact Disc Read-Only Memory (CD-ROM), a digital versatile disc-ROM (DVD-ROM), or another suitable computer-readable information recording medium. In addition, the application software may be provided via various information communication networks, such as the Internet. Alternatively, the monitoring/monitor apparatus 1 may be implemented by so-called cloud computing, in which functions of the monitoring/monitor apparatus 1 are provided by a remote server via an information communication network. The robot controlling apparatus 2 may be integrated with or provided separately from the robot 3 herein. The robot controlling apparatus 2 is connected to the monitoring/monitor apparatus 1 by an operation command communication cable 2*a*. The monitoring apparatus 1*j* and the protocol chart monitor apparatus 1*k* may be separate dedicated devices, or at least one of the monitoring apparatus 1*j* and the protocol chart monitor apparatus 1*k* may be implemented by a separate commercially available computer.

In this example, the image capturing apparatus 9 includes a full-view image capturing unit 9*a* and a partial-view image capturing unit 9*b*. The full-view image capturing unit 9*a* includes two cameras each of which captures a full-view moving image of a series of processes performed in an experiment. The partial-view image capturing unit 9*b* includes a camera that captures a partial-view moving image of each of the processes. The full-view image capturing unit 9*a* and the partial-view image capturing unit 9*b* are connected to the monitoring/monitor apparatus 1 by a captured information communication cable 9*c*. The units of the image capturing apparatus 9 need not be independent units. For example, a monitor camera mounted in the robot 3 may be used as the partial-view image capturing unit 9*b*.

The robot 3 is an articulated robot and performs a process on an object. For example, the robot 3 is capable of handling laboratory instruments (some are illustrated and some are not), such as holding and operating a pipette 4 with its arm. The robot 3 is also capable of moving various containers (some are illustrated and some are not), such as holding a microtube 6 stored in a tube rack 5 and moving the microtube 6 from the tube rack 5 to a main rack 7 or the like. In the embodiment, when the robot 3 performs a process using the microtube 6, such as putting an object into the microtube 6, the robot 3 moves the microtube 6 to the main rack 7 and performs the process at the main rack 7. The processing system 200 may further include various devices, such as a vortex mixer 8. FIG. 1 illustrates examples of other instruments used in an experiment, such as a dish rack that stores petri dishes, a centrifuge, and a magnetic rack. Note that the robot 3 is not limited to the illustrated type and may be a robot of another type, such as a single-arm robot.

Figure 2:
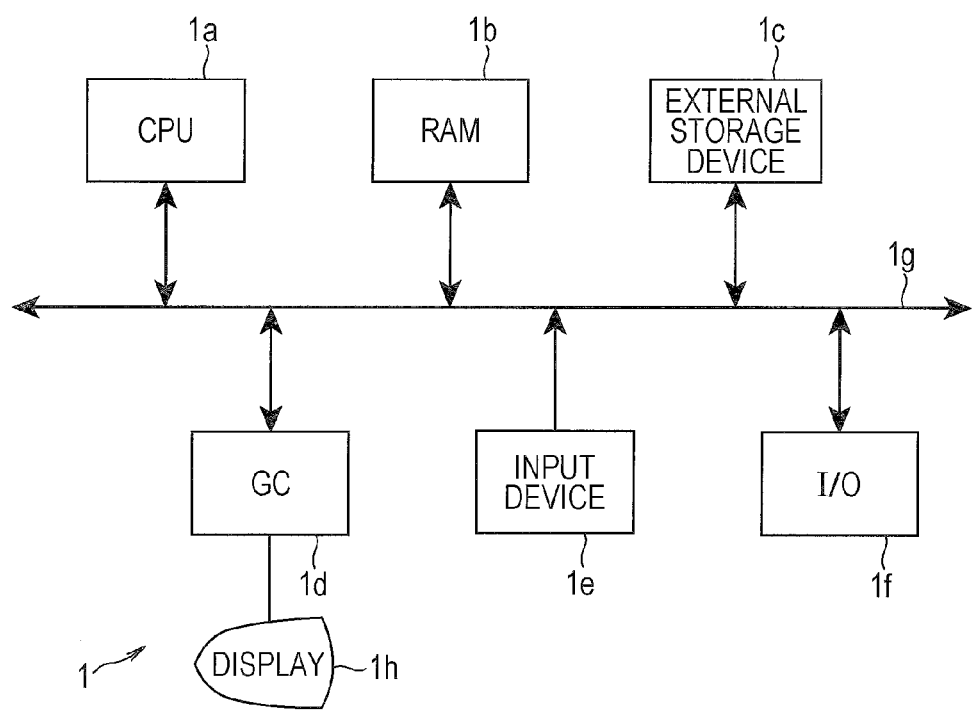
FIG. 2 is a block diagram illustrating a physical configuration of a monitoring apparatus and protocol chart monitor apparatus included in the processing system according to the embodiment of the disclosure.

FIG. 2 is a block diagram illustrating a physical configuration of the monitoring/monitor apparatus 1 according to the embodiment of the disclosure. FIG. 2 illustrates a configuration of a common computer used as the monitoring/monitor apparatus 1. The monitoring/monitor apparatus 1 includes a central processing unit (CPU) 1*a*, a random access memory (RAM) 1*b*, an external storage device 1*c*, a graphics controller (GC) 1*d*, an input device 1*e*, and an input/output (I/O) 1*f*, which are connected to one another by a data bus 1*g* to be able to mutually exchange electric signals. The external storage device 1*c* is a device, such as a hard disk drive (HDD) or a solid state drive (SSD), capable of storing information in a non-transitory manner. The external storage device 1*c* functions as a storage unit of the monitoring/monitor apparatus 1. The GC 1*d* is connected to a display 1*h*, such as a flat panel display, that allows the user to visually recognize an image. A signal is output from the GC 1*d* to the display 1*h*, and the display 1*h* displays an image based on the signal. The input device 1*e* is a device used by the user to input information, such as a keyboard, a mouse, or a touchscreen. The I/O 1f is an interface that allows the monitoring/monitor apparatus 1 to exchange information with an external device.

Figure 3:
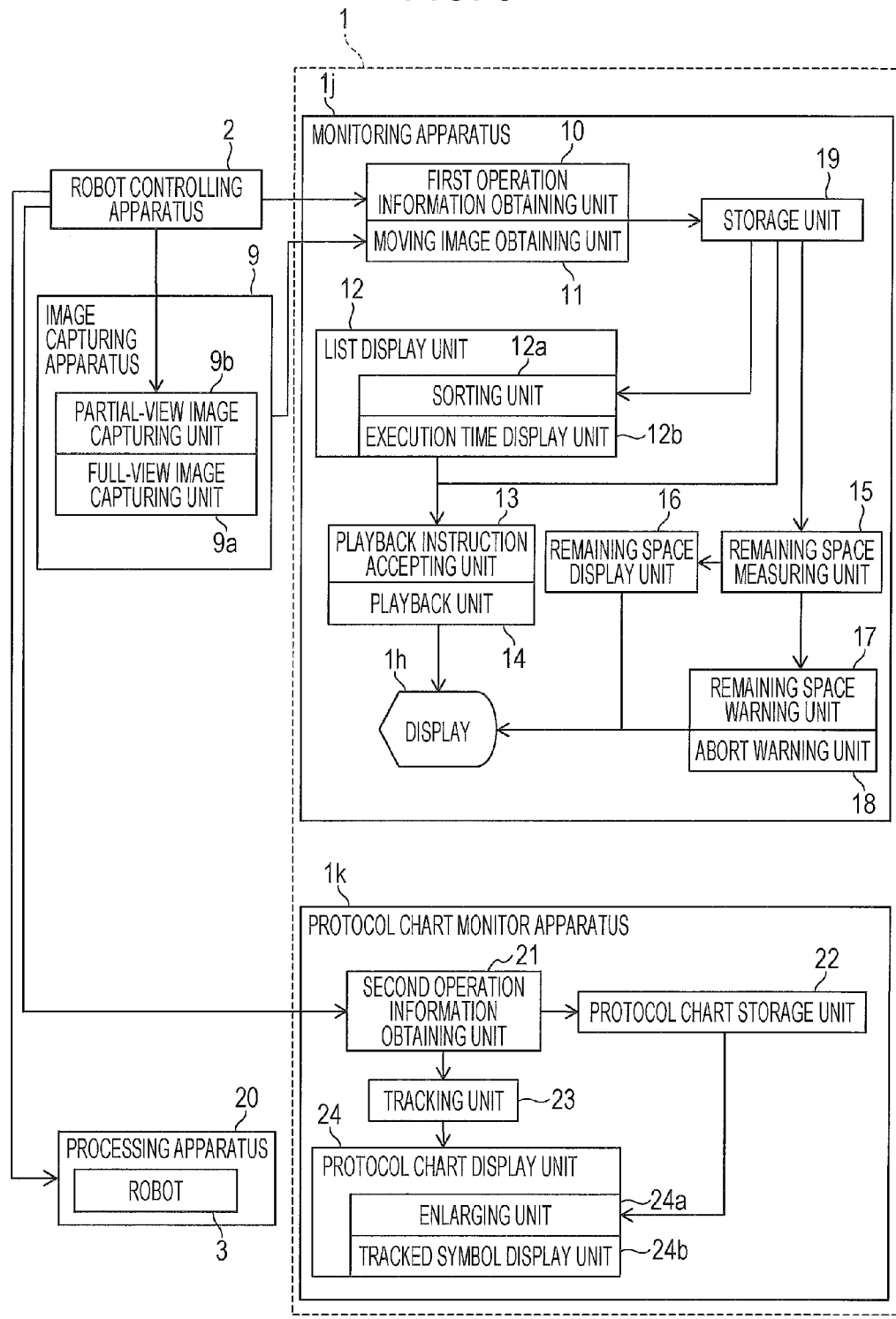
FIG. 3 is a functional block diagram of the monitoring apparatus and protocol chart monitor apparatus, a robot controlling apparatus, a processing apparatus, and an image capturing apparatus included in the processing system according to the embodiment of the disclosure.

FIG. 3 is a functional block diagram of the monitoring/monitor apparatus 1, the robot controlling apparatus 2, the image capturing apparatus 9, and the processing apparatus 20 that are included in the processing system 200 according to the embodiment. In FIG. 3, functional blocks are illustrated by focusing on functions of the monitoring/monitor apparatus 1 and the image capturing apparatus 9. Note that physical components having a one-to-one correspondence with the functional blocks are not necessarily present. Some functional blocks may be implemented as a result of an information processor, such as the CPU 1a of the monitoring/monitor apparatus 1, executing specific software, and some functional blocks may be implemented as a result of a specific storage space being allocated in an information storage device, such as the RAM 1b of the monitoring/monitor apparatus 1.

As described above, the image capturing apparatus 9 includes the full-view image capturing unit 9a and the partial-view image capturing unit 9b. The full-view image capturing unit 9a captures a full-view moving image of a series of processes performed on a container in an experiment. The partial-view image capturing unit 9b captures a partial-view moving image of each of the processes. The partial-view image capturing unit 9b performs image capturing at least while each of the processes is being performed.

As described above, the processing apparatus 20 includes the robot 3 that performs, in accordance with operation commands, processes on a container that contains an object to be processed in a field, such as biochemistry, biotechnology, or life science. The processing apparatus 20 may include peripheral devices, such as the vortex mixer 8, a centrifuge, a magnetic rack, a constant-temperature bath, and a constant-temperature chamber in addition to the robot 3. The robot 3 conducts an experiment by using such peripheral devices.

The monitoring apparatus 1j of the monitoring/monitor apparatus 1 includes a first operation information obtaining unit 10, a moving image obtaining unit 11, a list display unit 12, a playback instruction accepting unit 13, a playback unit 14, a remaining space measuring unit 15, a remaining space display unit 16, a remaining space warning unit 17, an abort warning unit 18, and a storage unit 19. The first operation information obtaining unit 10 obtains, from the robot controlling apparatus 2, operation information items, each of which is information concerning an operation of the robot 3. The moving image obtaining unit 11 obtains a moving image captured by the image capturing apparatus 9. The information obtained by the first operation information obtaining unit 10 and the moving image obtaining unit 11 is stored in the storage unit 19, which is constituted by the external storage device 1c, for example. The list display unit 12 displays at least one of a list of processes performed on a container or a list of operation information items of the robot 3. The playback instruction accepting unit 13 accepts an instruction to play a moving image corresponding to a specified process or a specified operation information item. The playback unit 14 plays the moving image from a timing corresponding to the specified process or the specified operation information item. The remaining space measuring unit 15 measures a remaining storage space of the storage unit 19 on the basis of the sizes of moving images and other data stored in the storage unit 19. The remaining space display unit 16 displays a remaining storage space of the storage unit 19. The remaining space warning unit 17 issues a warning concerning the remaining storage space of the storage unit 19 on the basis of the remaining storage space measured by the remaining space measuring unit 15. The abort warning unit 18 issues a warning indicating that image capturing performed by the image capturing apparatus 9 has been aborted, on the basis of the remaining storage space measured by the remaining space measuring unit 15.

The list display unit 12 may include a sorting unit 12a and an execution time display unit 12b. The sorting unit 12a rearranges at least one of the processes performed on the container and the operation information items of the robot 3. The execution time display unit 12b displays a time taken to perform each process on the container.

The protocol chart monitor apparatus 1k of the monitoring/monitor apparatus 1 includes a second operation information obtaining unit 21, a protocol chart storage unit 22, a tracking unit 23, and a protocol chart display unit 24. The second operation information obtaining unit 21 obtains, from the robot controlling apparatus 2, operation information items, each of which is information concerning an operation of the robot 3. The protocol chart storage unit 22 stores protocol charts. Each protocol chart includes at least one or more processing symbols each representing a corresponding process, and operation commands given to the robot 3 are generated from the protocol chart. When the robot 3 operates in accordance with operation commands, the tracking unit 23 tracks a processing symbol corresponding to an operation being performed by the robot 3 in the protocol chart. The protocol chart display unit 24 displays the protocol chart by indicating the processing symbol tracked by the tracking unit 23 when the robot 3 operates in accordance with operation commands.

The protocol chart display unit 24 includes an enlarging unit 24a and a tracked symbol display unit 24b. When the robot 3 operates in accordance with operation commands, the enlarging unit 24a displays a partial area of the protocol chart in an enlarged manner. The tracked symbol display unit 24b displays, when the enlarged partial area does not include the processing symbol tracked by the tracking unit 23, an indication of a position, in the protocol chart, of the processing symbol tracked by the tracking unit 23.

Herein, the term "operation command" refers to a single job or a job set constituted by a plurality of jobs and refers to a command that instructs a process to be performed, as one unit, on a container that contains an object. An operation command is generated in the following manner. Each symbol in a protocol chart is converted into jobs, which are units in which the robot 3 operates. Then, the resulting jobs are combined by taking an execution order of the jobs into account.

Figure 4:
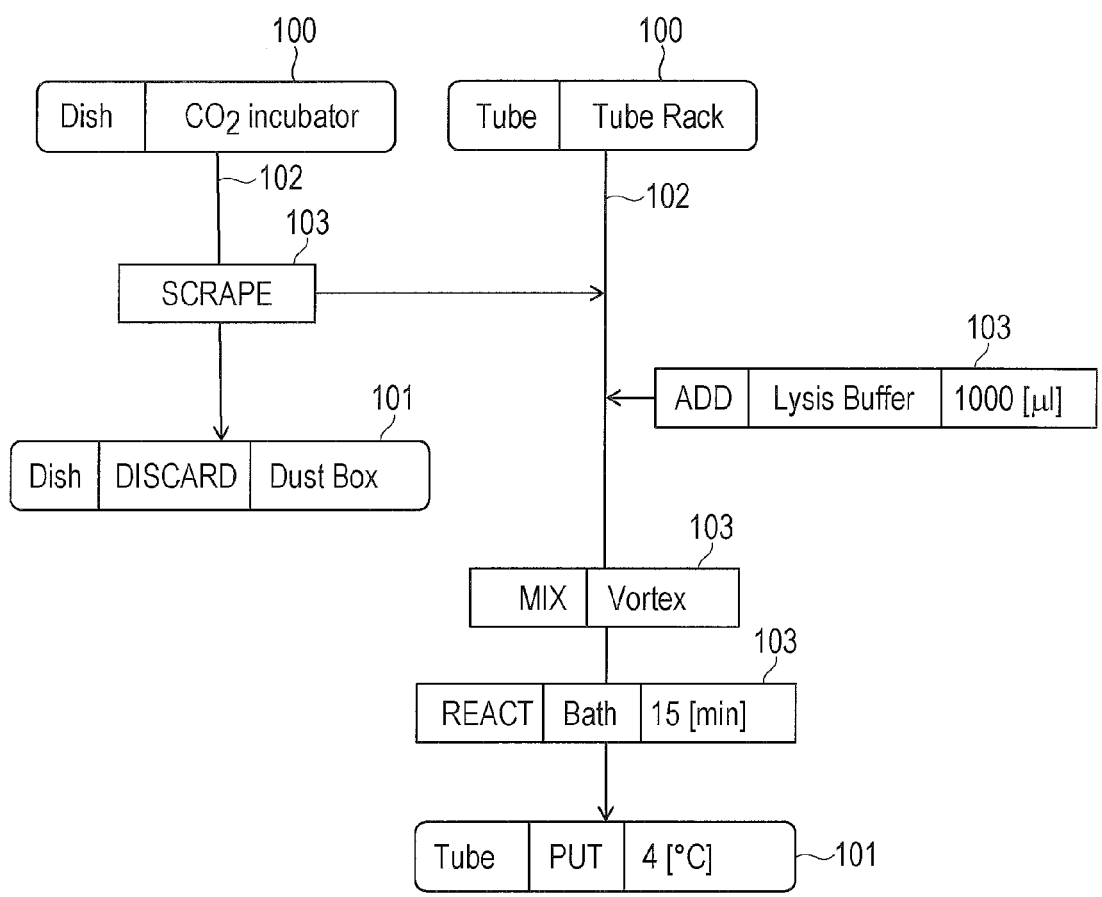
FIG. 4 illustrates an example of a protocol chart from which operation commands given to a robot according to the embodiment of the disclosure are generated.

FIG. 4 illustrates an example of a protocol chart from which operation commands given to the robot 3 according to the embodiment of the disclosure are generated.

Herein, the term "protocol chart" refers to a visually understandable illustration of a protocol. The term "protocol" refers to operation conditions and operation procedures, such as preprocessing, to be performed on an object in a field, such as biochemistry, biotechnology, or life science. The term "object" refers to a material subjected to an experiment in a field, such as biochemistry, biotechnology, or life science. The object may be, for example, a component of a biological tissue, such as cells or deoxyribonucleic acid (DNA). In addition, an experiment is performed on an object with the object being contained in an instrument especially suitable for the experiment, for example, a microtube (microcentrifuge tube), a petri dish (dish), or a microplate (microtiter plate). Herein, the term "container" refers to any of these instruments suitable for containing an object of the experiment. Herein, fields of biochemistry, biotechnology, and life science are mentioned; however, the field is not limited to these fields and may be another field.

In addition, for convenience, the up-down direction in FIG. 4 is referred to as a first direction, and a direction crossing the first direction is referred to as a second direction. An angle at which the first direction and the second direction cross each other is not necessarily a right angle. However, it is assumed herein that the first direction and the second direction cross at right angles. Accordingly, the second direction is the right-left direction in FIG. 4.

The protocol chart according to this example includes an initial symbol 100, a final symbol 101, an order line 102, and a processing symbol 103. The initial symbol 100 indicates an initial state of a container that contains an object. The final symbol 101 indicates a final state of the container. The processing symbol 103 indicates a process performed on the container. The order line 102 extends from the initial symbol 100 toward the final symbol 101. In a protocol chart, the initial symbol 100 and the final symbol 101 are basically arranged in the first direction and are connected by the order line 102 in the first direction. Along the order line 102, the processing symbol 103 is arranged. The example in FIG. 4 illustrates a set including the initial symbol 100 for "Dish", the corresponding final symbol 101, and the order line 102 connecting the initial symbol 100 and the final symbol 101 and a set including the initial symbol 100 for "Tube", the corresponding final symbol 101, and the order line 102 connecting the initial symbol 100 and the final symbol 101. The order line 102 indicates, by using an arrow, the order in which processes are performed. In addition, the initial symbol 100 for "Dish" indicates taking out a petri dish from a $CO_2$ incubator to prepare it for the following process, whereas the initial symbol 100 for "Tube" indicates taking out the microtube 6 from the tube rack 5 to prepare to perform the following process at the main rack 7. In addition, the final symbol 101 for "Dish" indicates a process of discarding, in a dust box, the petri dish for which the processes have been finished, whereas the final symbol 101 for "Tube" indicates a process of storing the microtube 6 containing the object in a constant-temperature chamber at 4° C.

The processing symbol 103 for "SCRAPE", which is connected to the initial symbol 100 for "Dish" by the order line 102, indicates a process (scraping process) of scraping the object, such as cells, cultured on the petri dish with a scraper. The processing symbol 103 for "SCRAPE" is attached with an arrow that indicates the destination to which the object is moved. The arrow indicates putting the scraped object in the microtube 6. The petri dish is then discarded, and a process indicated by the processing symbol 103 for "ADD" is performed for the microtube 6. The processing symbol 103 for "ADD" indicates a process of adding 1000 µl of lysis buffer to the microtube 6 containing the object. Then, a process indicated by the processing symbol 103 for "MIX" and a process indicated by the processing symbol 103 for "REACT" are performed for the microtube 6. Herein, the process indicated by the processing symbol 103 for "MIX" is a vortex process using the vortex mixer 8. The process indicated by the processing symbol 103 for "REACT" is a process of keeping the microtube 6 in a constant-temperature bath for 15 minutes. After such processes have been performed, the microtube 6 is stored in a constant-temperature chamber at 4° C.

Figure 5:
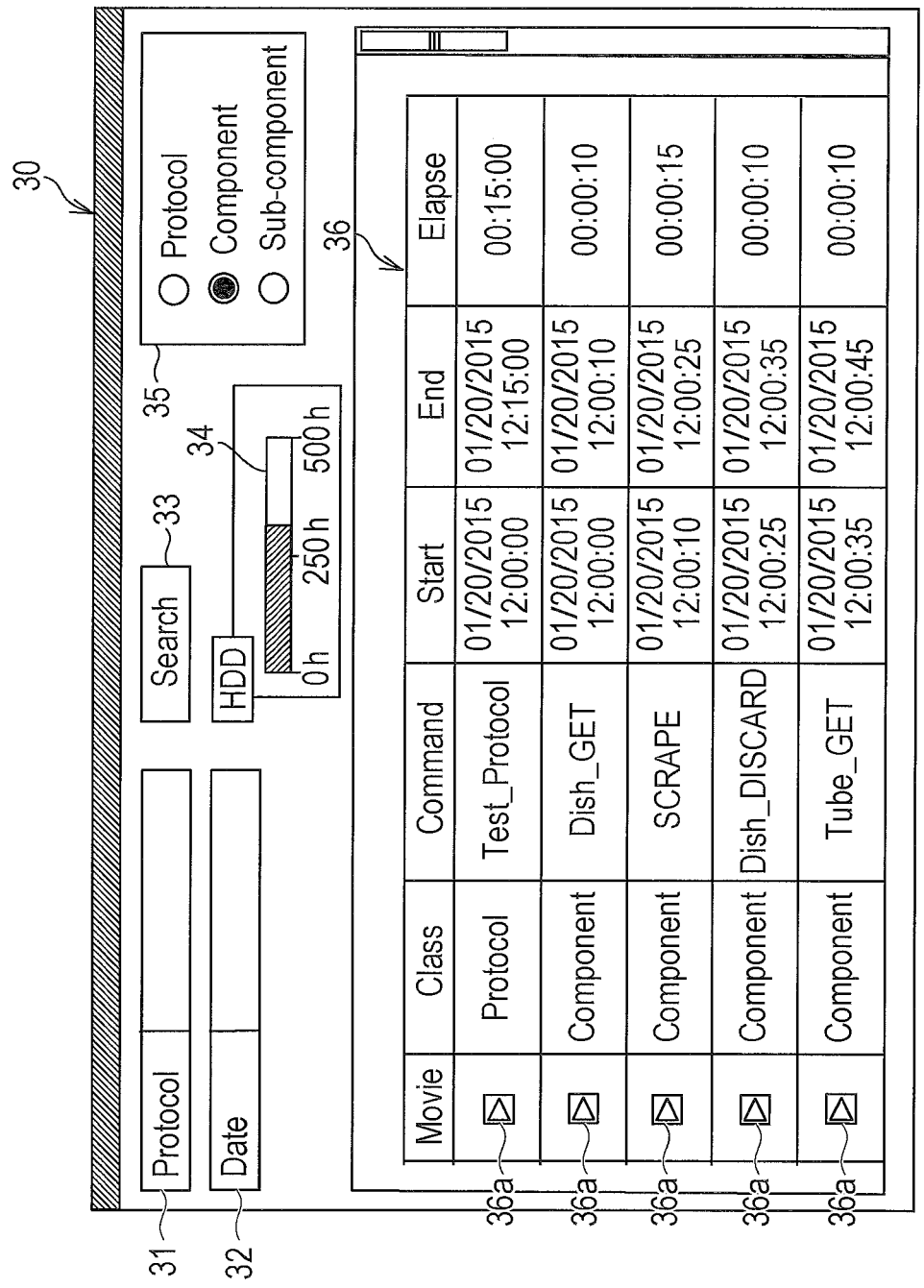
FIG. 5 illustrates an example of a list window displayed by a monitoring apparatus according to the embodiment of the disclosure.

FIG. 5 illustrates an example of a list window 30 displayed by the monitoring apparatus 1j according to the embodiment of the disclosure. The list window 30 is a window displayed by the list display unit 12. The list window 30 shows at least one of a list of processes performed on a container in the experiment and a list of operation information items of the robot 3. In this example, the list window 30 includes a protocol search box 31, an experiment date/time search box 32, a search button 33, a remaining space indication 34, a filtering button set 35, and an operation information list 36.

The protocol search box 31 is a search box used for searching for operation information items stored in the storage unit 19. The protocol search box 31 is used to perform a search based on the protocol name. The experiment date/time search box 32 is a search box for searching for an operation information item stored in the storage unit 19. The experiment date/time search box 32 is used to perform a search based on the date/time at which the operation information item has been obtained by the first operation information obtaining unit 10. A search using the protocol search box 31 or the experiment date/time search box 32 is selectively performed in response to pressing of the search button 33.

As described above, the monitoring apparatus 1j according to the embodiment includes the remaining space measuring unit 15 that measures the remaining storage space of the storage unit 19 and the remaining space display unit 16 that displays the remaining storage space. The remaining space indication 34 is displayed by the remaining space display unit 16 and indicates the remaining storage space of the storage unit 19. In this example, the remaining space indication 34 indicates that more than half of the storage capacity of the storage unit 19 is left and that recording can be continuously performed for more than 250 hours. The remaining space display unit 16 allows a timing when the remaining storage space of the storage unit 19 runs short (for example, becomes less than a certain reference) to be estimated and an action, such as preparing an additional storage capacity in advance, to be taken.

The filtering button set 35 includes radio buttons for changing the class of operation information items displayed in the operation information list 36. In this example, a button "Component" is selected. Herein, the term "Component" refers to each processing component that is included in a protocol of an experiment and that respectively corresponds to a processing symbol in the protocol chart. The operation information list 36 illustrated in FIG. 5 shows, for each processing component, an operation information item of the robot 3 obtained when the robot 3 conducts an experiment in accordance with operation commands generated based on the protocol chart illustrated in FIG. 4.

Suppose that a button "Protocol" is selected from the filtering button set 35. In such a case, the operation information list 36 displays the protocol names alone but does not display a list of processing components included in each protocol. In addition, suppose that a button "Sub-component" is selected from the filtering button set 35. In such a case, the operation information list 36 displays sub-components of each processing component corresponding to a processing symbol. The sub-components of each processing component indicate specific operations performed by the robot 3 to carry out the processing component. For example, the sub-components of each processing component indicate processing such as moving the arm of the robot 3 by a certain distance, holding an instrument with the arm, and replacing the tip of the pipette 4. Permitting selection of the class of processing to be displayed makes it possible to display a list of operation information items in accordance with a purpose, such as grasping the overview of the experiment or details of the experiment.

At the topmost row of the operation information list 36, "Protocol" is displayed at a field "Class", and "Test_Protocol", which is the protocol name, is displayed at a field "Command". This protocol is a protocol carried out in accordance with the protocol chart illustrated in FIG. 4. At the topmost row of the operation information list 36, it is also indicated that the start time and the end time of execution of the protocol are 12:00:00 on Jan. 20, 2015 ("Start") and 12:15:00 on Jan. 20, 2015 ("End"), respectively and that the execution time of the protocol is 15 minutes ("Elapse"). Herein, the term "execution time" refers to a time taken for each process or a time taken for an operation indicated by each operation information item. The execution time is displayed by the execution time display unit 12b. In this example, a time taken for processing is shown for each processing component for a corresponding one of the processing symbols in the protocol chart. In addition, in the case where the button "Sub-component" is selected from the filtering button set 35, a time taken for each sub-component of each processing component is displayed as the execution time. This configuration allows the user of the monitoring apparatus 1j to check a time taken for the entire protocol, a time taken for each processing component, and a time taken for each sub-component of each processing component.

The image capturing apparatus 9 according to the embodiment continuously captures a moving image of a series of processes performed in the experiment. The storage unit 19 of the monitoring apparatus 1j stores the moving image captured by the image capturing apparatus 9. At that time, an operation information item of the robot 3 and a timing at which a process performed by the robot 3 in relation to the operation information item is recorded in the moving image can be associated with each other. This association enables a corresponding start point in the moving image to be identified based on a process performed by the robot 3 or an operation information item and, thus, enables the moving image to be played from a timing corresponding to the process or the operation information item. This association may be made by comparing the operation time recorded in the operation information item and the time recorded in the moving image with each other. Alternatively, the association may be made according to another method, such as recording, every time an operation information item is generated, bookmark information corresponding to the operation information item, that is, information for identifying the operation information item and the playback point in the moving image, in the moving image. The moving images and the operation information items of the robot 3 that are stored in such a manner are sorted by the sorting unit 12a in a predetermined order and are collectively displayed as the operation information list 36. The predetermined order may be, for example, a chronological order. In addition, another type of order may be made selectable. At each row of the operation information list 36 displayed by the monitoring apparatus 1j according to the embodiment, a playback button 36a is displayed. The playback instruction accepting unit 13 accepts an instruction to play a moving image corresponding to a specified process or a specified operation information item. The playback unit 14 then plays the moving image from a timing corresponding to the specified process or the specified operation information item. For example, suppose that the playback button 36a displayed at the topmost row of the operation information list 36 is selected with a pointing device, such as a mouse. In such a case, the playback unit 14 plays a 15-minute-long moving image captured by the image capturing apparatus 9 from the start to the end of the protocol "Test_Protocol".

At a second row of the operation information list 36, an operation information item of a process corresponding to the initial symbol 100 for "Dish" is displayed. The "Class" of this process is "Component", and the "Command" of this process is "Dish_GET". The start time and the end time of this process are 12:00:00 on Jan. 20, 2015 ("Start") and 12:00:10 on Jan. 20, 2015 (End), respectively, and the execution time of this process is 10 seconds ("Elapse"). In response to selection of the playback button 36a displayed at the second row of the operation information list 36, the playback unit 14 plays at least a 10-second-long moving image obtained as a result of the image capturing apparatus 9 capturing a moving image of the robot 3 holding the petri dish to prepare it for the following process. In this example, the playback unit 14 finishes playing the moving image after playing the 10-second-long moving image corresponding to "Dish_GET"; however, playback of the moving image may be continued to the following one.

At a third row of the operation information list 36, an operation information item of a process corresponding to the processing symbol 103 for "SCRAPE" is displayed. The "Class" of this process is "Component", and the "Command" of this process is "SCRAPE". The start time and the end time of this process are 12:00:10 on Jan. 20, 2015 ("Start") and 12:00:25 on Jan. 20, 2015 ("End"), respectively, and the execution time of this process is 15 seconds ("Elapse"). In response to selection of the playback button 36a displayed at the third row of the operation information list 36, the playback unit 14 plays a 15-second-long moving image obtained as a result of the image capturing apparatus 9 capturing a moving image of the process in which the robot 3 holds a scraper with its arm and scrapes cells cultured on the petri dish.

As described above, the image capturing apparatus 9 according to the embodiment includes the full-view image capturing unit 9a that captures a full-view moving image of a series of processes performed in an experiment and the partial-view image capturing unit 9b that captures a partial-view moving image of each of the processes. The full-view image capturing unit 9a according to the embodiment continuously captures a moving image of all the processes of the experiment from the start to the end of the experiment. In contrast, the partial-view image capturing unit 9b performs image capturing at least while each process is being performed. Specifically, the partial-view image capturing unit 9b reads an operation command sent from the robot controlling apparatus 2 to the robot 3, starts capturing the partial-view moving image at a timing at which the robot 3 starts a corresponding process, and finishes capturing the partial-view moving image at a timing at which the robot 3 finishes the process. For example, in the case of the process corresponding to the processing symbol 103 for "SCRAPE", the partial-view image capturing unit 9b captures, in close up, a moving image of the robot 3 holding the petri dish and scraping cells by using a scraper. As a result of both a full-view moving image and a partial-view moving image of processing performed in the experiment being captured in this way, both the overview and details of the experiment are recorded. In addition, the storage capacity may be saved by limiting a period for which the partial-view image capturing unit 9b captures a moving image to a period for which each process is being performed. In the embodiment, a full-view moving image is captured with two cameras, whereas a partial-view moving image is captured with one camera. However, the numbers of cameras used may be changed.

The playback instruction accepting unit 13 accepts an instruction to play both the moving image captured by the full-view image capturing unit 9a and the moving image captured by the partial-view image capturing unit 9b. In response to the user selecting the playback button 36a, the playback unit 14 plays both the moving image captured by the full-view image capturing unit 9a and the moving image captured by the partial-view image capturing unit 9b. The playback instruction accepting unit 13 may separately accept an instruction to play the moving image captured by the full-view image capturing unit 9a and an instruction to play the moving image captured by the partial-view image capturing unit 9b. In addition, the playback unit 14 may separately play each of the moving images. In such a case, two or more playback buttons for the full-view moving image and the partial-view moving image may be displayed in the operation information list 36.

At a fourth row of the operation information list 36, an operation information item of a process corresponding to the final symbol 101 for "Dish" is displayed. The "Class" of this process is "Component", and the "Command" of this process is "Dish_DISCARD". The start time and the end time of this process are 12:00:25 on Jan. 20, 2015 ("Start") and 12:00:35 on Jan. 20, 2015 ("End"), respectively, and the execution time of this process is 10 seconds ("Elapse"). In response to selection of the playback button 36a displayed at the fourth row of the operation information list 36, the playback unit 14 plays a 10-second-long moving image obtained as a result of the image capturing apparatus 9 capturing a moving image of the robot 3 discarding the petri dish held thereby in the dust box.

At a fifth row of the operation information list 36, an operation information item of a process corresponding to the initial symbol 100 for "Tube" is displayed. The "Class" of this process is "Component", and the "Command" of this process is "Tube_GET". The start time and the end time of this process are 12:00:35 on Jan. 20, 2015 ("Start") and 12:00:45 on Jan. 20, 2015 ("End"), respectively, and the execution time of this process is 10 seconds ("Elapse"). In response to selection of the playback button 36a displayed at the fifth row of the operation information list 36, the playback unit 14 plays a 10-second-long moving image obtained as a result of the image capturing apparatus 9 capturing a moving image of the robot 3 holding the microtube 6 and moving the microtube 6 to the main rack 7 to prepare it for the following process.

As described above, the monitoring apparatus 1j according to the embodiment presents, in an easy-to-grasp manner for a third party, an objective evidence indicating that the protocol has been carried out by the robot 3 by displaying a list including the operation information items of the robot 3 and the moving images captured by the image capturing apparatus 9 in relation to the respective operation information items. Because all the processes of the experiment are continuously captured by the full-view image capturing unit 9a, situations where part of the experiment is not recorded in the moving image or the moving image is intentionally edited or falsified may be avoided with the image capturing apparatus 9. In addition, because the close-up image of each process is captured by the partial-view image capturing unit 9b, it becomes easier to analyze and verify the contents of the experiment later.

The user of the monitoring apparatus 1j can search for a protocol carried out in the past and play a moving image of the protocol from the start of each process. Accordingly, it becomes easier to find a point to be improved in each process when the protocol is improved. In addition, when the series of processes is used in another protocol, the other protocol may be smoothly designed by checking the moving image of the series of processes.

Figure 6:
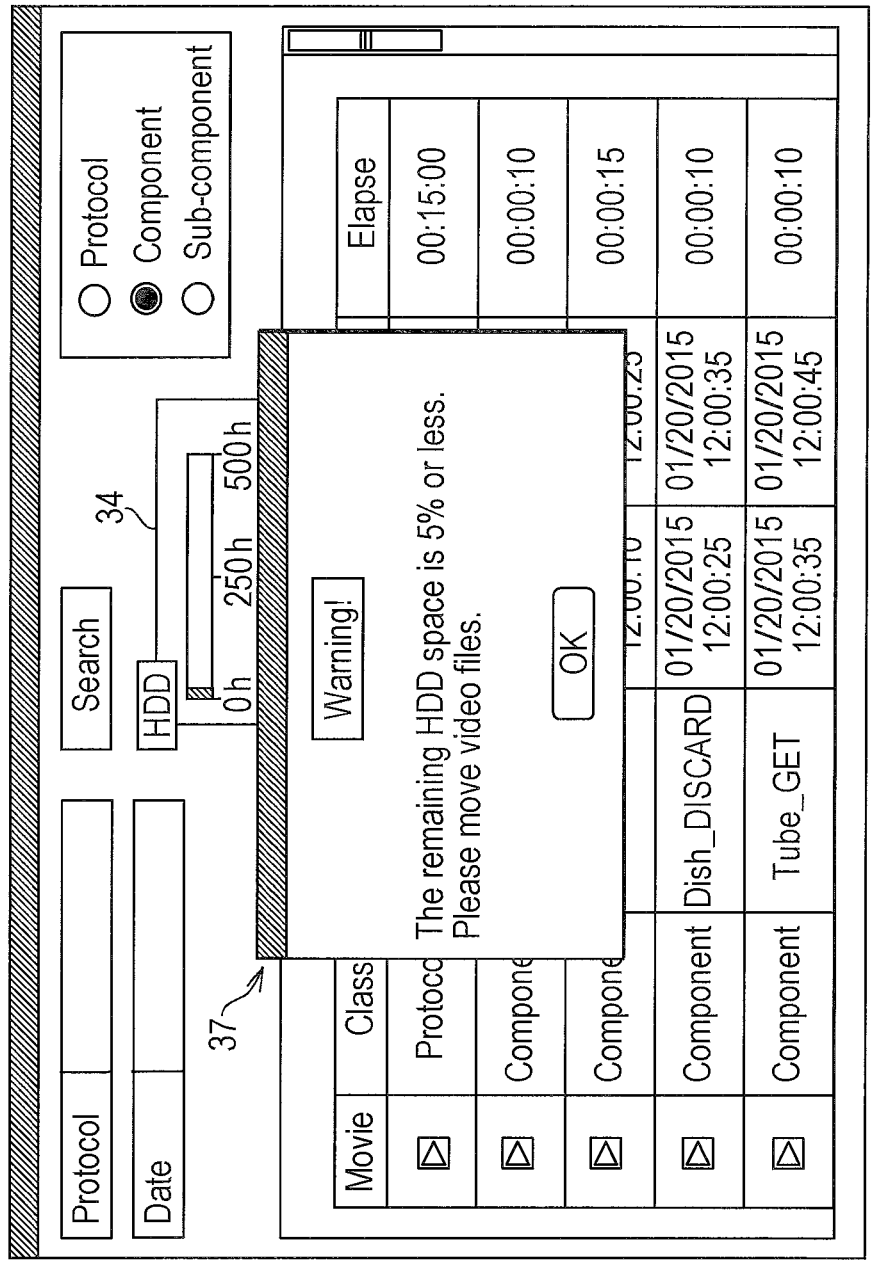
FIG. 6 illustrates an example of a remaining space warning displayed by the monitoring apparatus according to the embodiment of the disclosure.

FIG. 6 illustrates an example of a remaining space warning 37 displayed by the monitoring apparatus 1j according to the embodiment of the disclosure. The remaining space warning unit 17 of the monitoring apparatus 1j according to the embodiment issues a warning concerning the remaining storage space of the storage unit 19 on the basis of the remaining storage space measured by the remaining space measuring unit 15. In the example illustrated in FIG. 6, the remaining space indication 34 indicates that there is a little storage space left. Specifically, the remaining space indication 34 indicates that the remaining storage space is 5% of the entire storage capacity. Accordingly, in the case where the storage unit 19 is constituted by a hard disk drive (HDD), for example, the remaining space warning unit 17 issues a warning to the user of the monitoring apparatus 1j by displaying the remaining space warning 37 including a message "The remaining HDD space is 5% or less. Please move video files." over the operation information list 36. With such a configuration, a situation is avoided where the remaining storage space of the storage unit 19 is used up and, consequently, the moving image captured by the image capturing apparatus 9 and the operation information items of the robot 3 obtained from the robot controlling apparatus 2 can no longer be stored.

Figure 7:
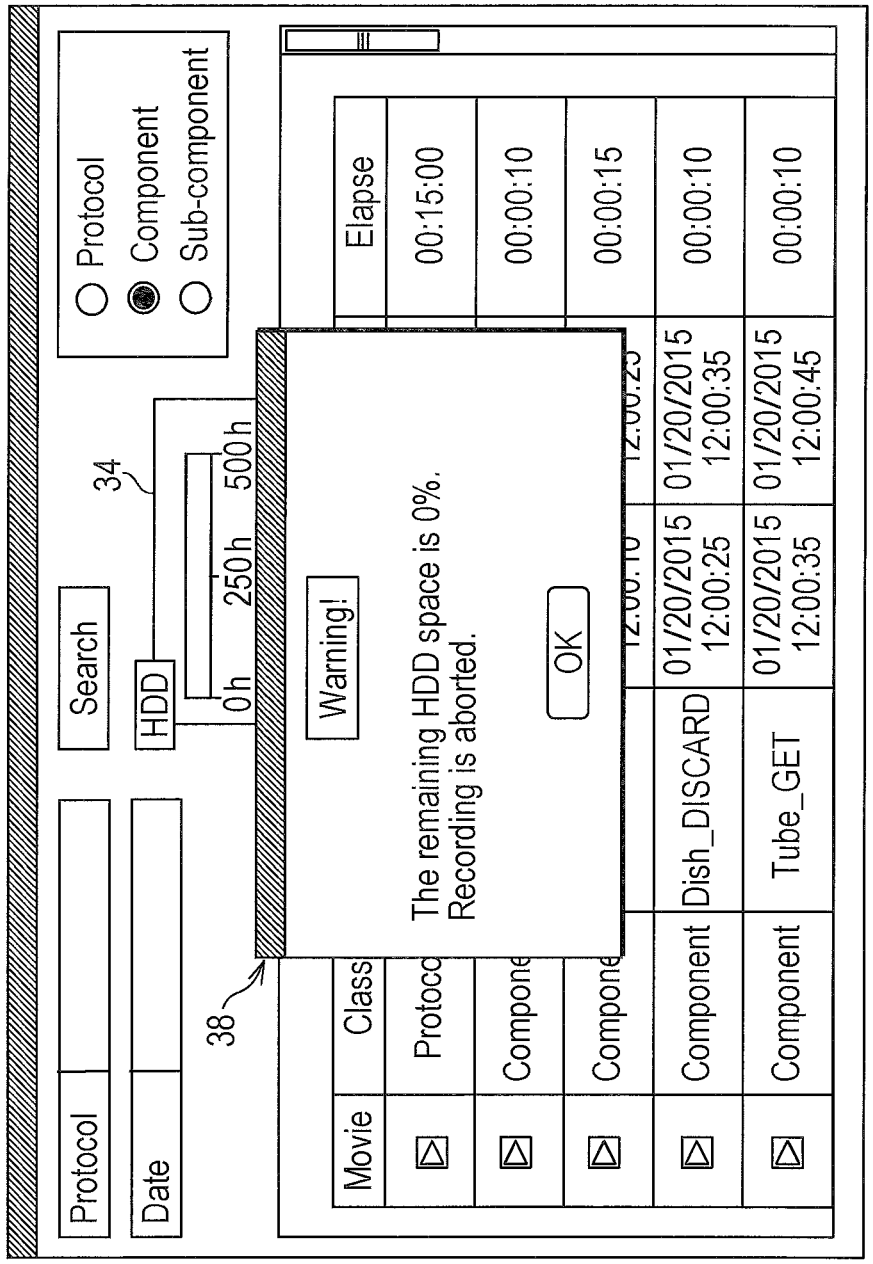
FIG. 7 illustrates an example of an abort warning displayed by the monitoring apparatus according to the embodiment of the disclosure.

FIG. 7 illustrates an example of an abort warning 38 displayed by the monitoring apparatus 1j according to the embodiment of the disclosure. The abort warning unit 18 of the monitoring apparatus 1j according to the embodiment issues a warning indicating that image capturing performed by the image capturing apparatus 9 has been aborted, on the basis of the remaining storage space measured by the remaining space measuring unit 15. In the example illustrated in FIG. 7, the remaining space indication 34 indicates that there is no remaining storage space (0%). Accordingly, even if the image capturing apparatus 9 captures a moving image, the moving image can no longer be stored in the external storage device 1c. Accordingly, the abort warning unit 18 issues a warning to the user of the monitoring apparatus 1j by displaying the abort warning 38 including a message "The remaining HDD space is 0%. Recording is aborted." over the operation information list 36. Even in the case where image capturing performed by the image capturing apparatus 9 has been aborted, the experiment being performed is continued to the end instead of being aborted in the processing system 200 according to the embodiment. Note that a configuration may be made such that, when there is no remaining storage space, an abort command for making a new experiment not be performed may be sent from the monitoring apparatus 1j to the robot controlling apparatus 2. By employing such a configuration, there is no experiment for which a moving image is not recorded, and an objective evidence of actually performed processing is obtained for all experiments.

Figure 8:
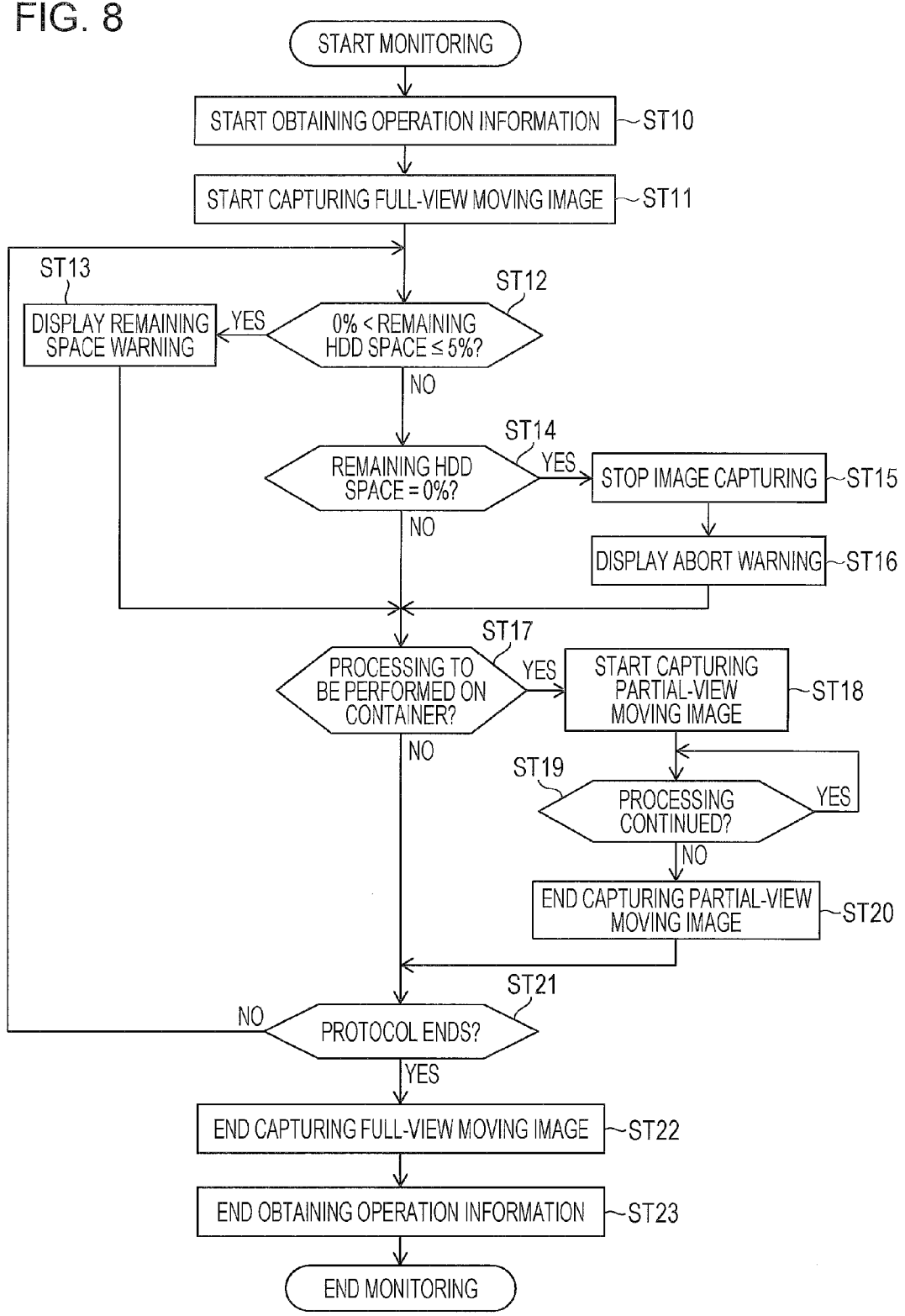
FIG. 8 is a flowchart of a monitoring process performed by the monitoring apparatus according to the embodiment of the disclosure.

FIG. 8 is a flowchart of a monitoring process performed by the monitoring apparatus 1j according to the embodiment of the disclosure. The monitoring apparatus 1j starts the monitoring process when a protocol is started by the processing system 200. The first operation information obtaining unit 10 of the monitoring apparatus 1j first starts obtaining an operation information item from the robot controlling apparatus 2 (ST10). The full-view image capturing unit 9a of the image capturing apparatus 9 then starts capturing a full-view moving image of a series of processes (ST11). The moving image obtaining unit 11 then obtains the captured moving image.

While the protocol is being carried out, the monitoring apparatus 1*j* stores the operation information items and the moving image. The remaining space measuring unit 15 measures a remaining storage space of the storage unit 19 and determines whether the remaining storage space of the storage unit 19 (for example, an HDD) is greater than 0% and less than or equal to 5% of the entire storage capacity of the storage unit 19 (ST12). If the remaining storage space of the storage unit 19 is greater than 0% and less than or equal to 5% (YES in ST12), the remaining space warning unit 17 displays the remaining space warning 37 (ST13).

If the remaining storage space of the storage unit 19 is greater than 5% or is equal to 0% (NO in ST12), the process proceeds from ST12 to ST14. The remaining space measuring unit 15 determines whether the remaining storage space of the storage unit 19 is 0% (ST14). If the remaining storage space of the storage unit 19 is 0% (YES in ST14), image capturing performed by the image capturing apparatus 9 is aborted (ST15). The abort warning unit 18 then displays the abort warning 38 (ST16).

The monitoring apparatus 1*j* then determines whether a process is to be performed on a container, based on the operation information item obtained from the robot controlling apparatus 2 (ST17). If it is determined that a process is to be performed on the container (YES in ST17), the partial-view image capturing unit 9*b* starts capturing a partial-view moving image of the process (ST18). Capturing of the partial-view moving image is performed while the process is continued (YES in ST19), and ends (ST20) upon the process ends (NO in ST19).

Finally, the monitoring apparatus 1*j* determines whether the protocol has ended (ST21). If it is determined that the protocol has ended (YES in ST21), the full-view image capturing unit 9*a* finishes capturing the full-view moving image (ST22). The first operation information obtaining unit 10 then finishes obtaining the operation information item (ST23).

Figure 9:
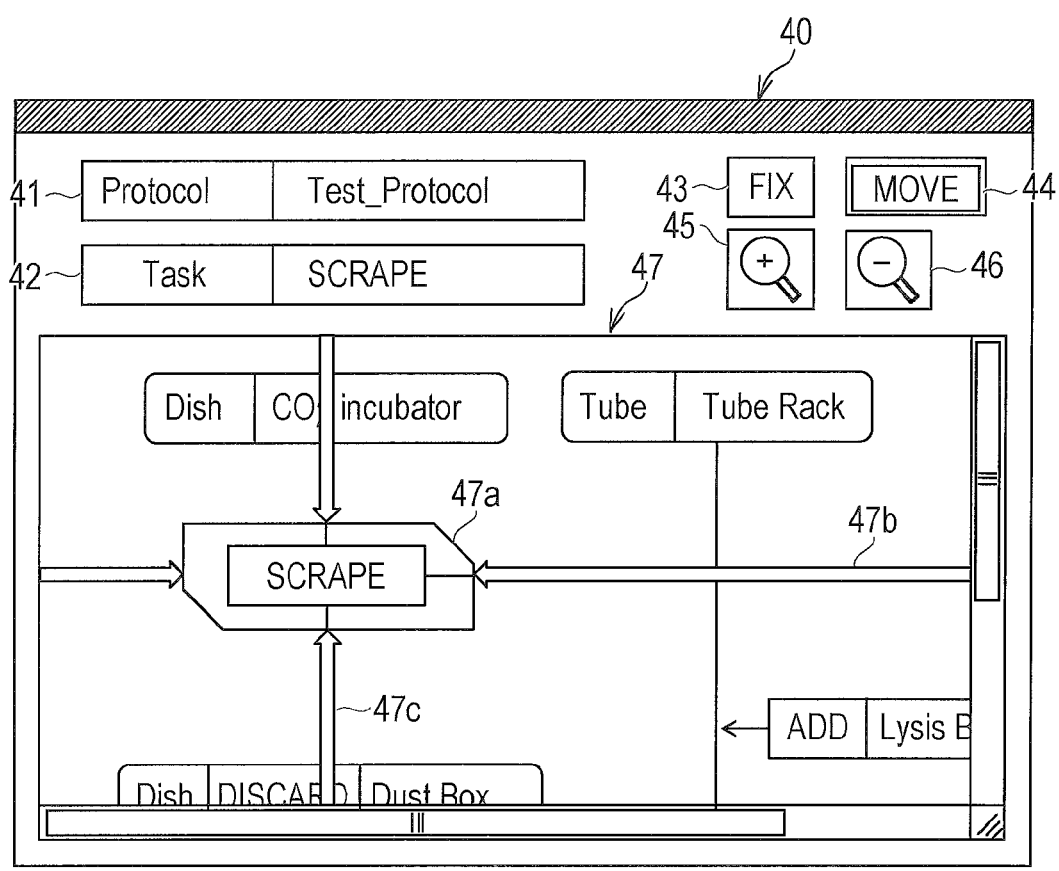
FIG. 9 illustrates a first example of a protocol chart monitor window displayed by the protocol chart monitor apparatus according to the embodiment of the disclosure.

FIG. 9 illustrates a first example of a protocol chart monitor window 40 displayed by the protocol chart monitor apparatus 1*k* according to the embodiment of the disclosure. When a protocol is carried out by the robot 3, the protocol chart monitor apparatus 1*k* according to the embodiment reads, from the protocol chart storage unit 22, the protocol chart from which operation commands given to the robot 3 are generated. The protocol chart display unit 24 then displays the protocol chart on the display 1*h* to indicate the progress of the protocol. The protocol chart storage unit 22 may store a protocol chart in association with operation information items of the robot 3. The operation information items are obtained by the second operation information obtaining unit 21. In this example, it is assumed that at least the protocol chart illustrated in FIG. 4 is stored in the protocol chart storage unit 22 in association with operation information items.

The protocol chart monitor window 40 of this example includes a protocol-being-executed display box 41, a processing-symbol-being-executed display box 42, a fix button 43, a move button 44, an enlarge button 45, a reduce button 46, and a protocol chart display area 47. The protocol-being-executed display box 41 displays "Test_Protocol", which is the name of the protocol being executed. In addition, the processing-symbol-being-executed display box 42 displays the name of the processing symbol corresponding to the process being executed by the robot 3, that is, "SCRAPE" in this example.

In this example, the move button 44 is selected. When the move button 44 is selected, part of the protocol chart or the entire protocol chart selected by the user is displayed at the protocol chart display area 47. In contrast, when the fix button 43 is selected, a tracked symbol 47*a* (described later) is displayed substantially at the center of the protocol chart display area 47 in a fixed manner.

As described above, the protocol chart monitor apparatus 1*k* according to the embodiment includes the enlarging unit 24*a* that displays a partial area of the protocol chart in an enlarged manner when the robot 3 operates in accordance with operation commands. In this example, a partial area of the protocol chart is displayed in an enlarged manner at the protocol chart display area 47 of the protocol chart monitor window 40. The protocol chart displayed at the protocol chart display area 47 can be enlarged or reduced by operating the enlarge button 45 or the reduce button 46. Displaying a part of the protocol chart in an enlarged manner with the enlarge button 45 allows the user to grasp details concerning the processing symbol corresponding to the process being executed. In addition, the reduce button 46 allows the user to grasp the overview of the protocol chart and grasp the flow of the protocol.

When the robot 3 operates in accordance with operation commands, the protocol chart display unit 24 displays the protocol chart by indicating the processing symbol tracked by the tracking unit 23. The tracking unit 23 tracks a processing symbol, in the protocol chart, corresponding to an operation being performed by the robot 3 when the robot 3 operates in accordance with operation commands. In this example, the tracked symbol 47*a*, a first arrow 47*b*, and a second arrow 47*c* are displayed over the protocol chart displayed at the protocol chart display area 47. The tracked symbol 47*a* surrounds the processing symbol tracked by the tracking unit 23 (the processing symbol 103 for "SCRAPE" in this example). The first arrow 47*b* and the second arrow 47*c* indicate the position of the tracked symbol 47*a* with respect to the first direction (the up-down direction in FIG. 9) and the second direction (the left-right direction in FIG. 9), respectively. The protocol chart monitor apparatus 1*k* according to the embodiment displays the tracked symbol 47*a* and other display components, thereby allowing the user to visually grasp which process the robot 3 is being performing from among the processes included in the protocol.

Figure 10:
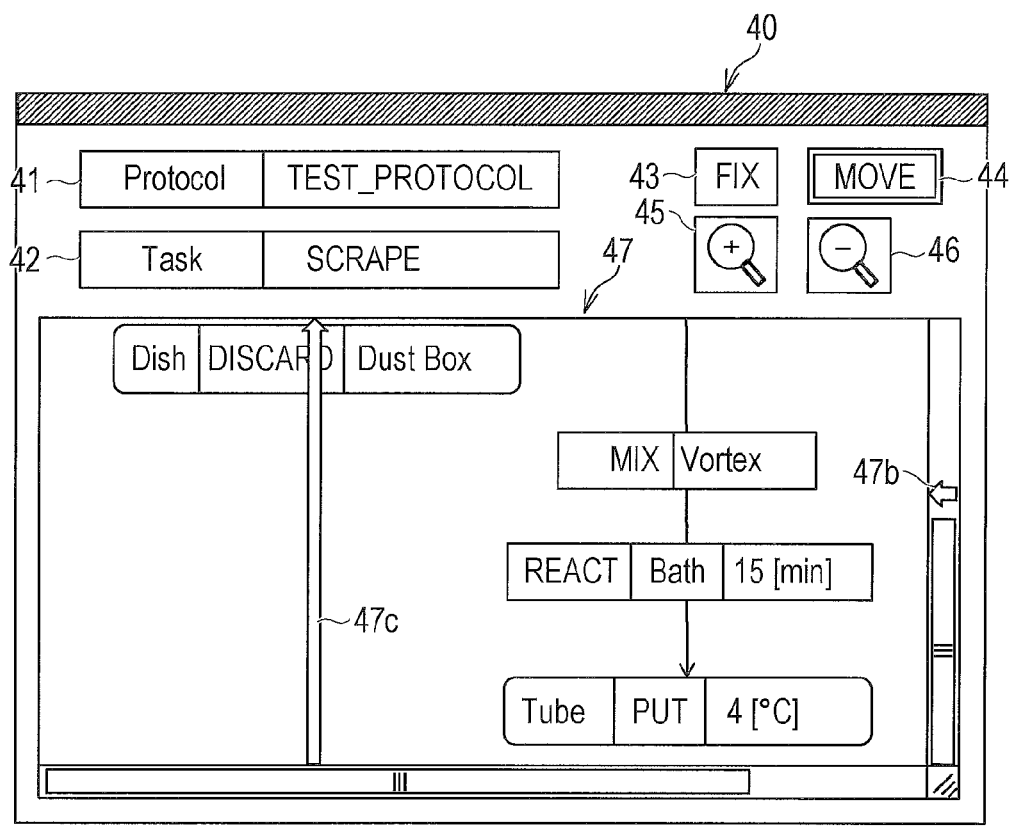
FIG. 10 illustrates a second example of the protocol chart monitor window displayed by the protocol chart monitor apparatus according to the embodiment of the disclosure.

FIG. 10 illustrates a second example of the protocol chart monitor window 40 displayed by the protocol chart monitor apparatus 1*k* according to the embodiment of the disclosure. The protocol chart displayed at the protocol chart display area 47 in this example is similar to that of the first example of the protocol chart monitor window 40; however, the part of the protocol chart displayed at the protocol chart display area 47 does not include the processing symbol tracked by the tracking unit 23 (the processing symbol 103 for "SCRAPE"). Other configurations of the protocol chart monitor window 40 of the second example are the same as those of the first example.

When the processing symbol tracked by the tracking unit 23 is not included in the area that is displayed by the enlarging unit 24*a* in an enlarged manner, the tracked symbol display unit 24*b* displays an indication of a position, in the protocol chart, of the processing symbol tracked by the tracking unit 23. In this example, the first arrow 47*b* is disposed at a scrollbar of the protocol chart display area 47 to indicate the position of the processing symbol tracked by the tracking unit 23 in the first direction (the up-down direction in FIG. 10). In addition, the second arrow 47c indicates the position of the processing symbol tracked by the tracking unit 23 in the second direction (the left-right direction in FIG. 10). As described above, even when the processing symbol tracked by the tracking unit 23 is not displayed at the protocol chart display area 47, the protocol chart monitor apparatus 1k according to the embodiment allows the user to grasp the position, in the protocol chart, of the processing symbol corresponding to the process being executed.

Figure 11:
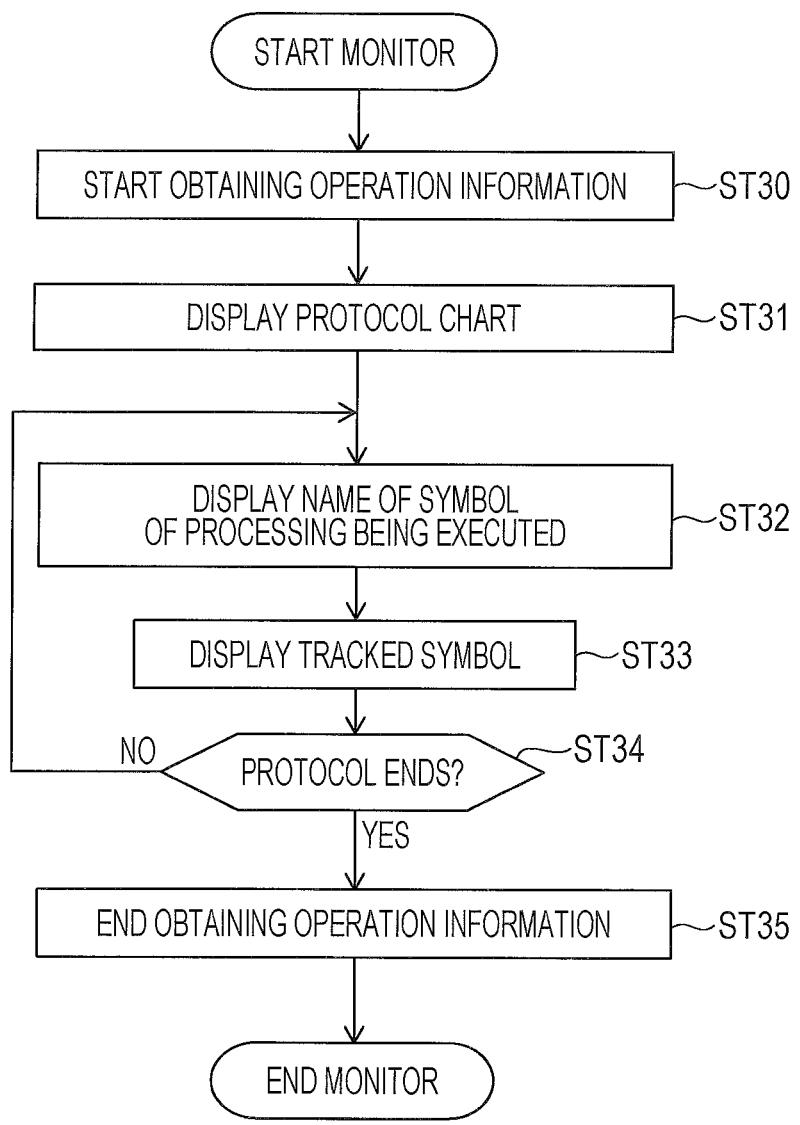
FIG. 11 is a flowchart of a monitor process performed by the protocol chart monitor apparatus according to the embodiment of the disclosure.

FIG. 11 is a flowchart of a monitor process performed by the protocol chart monitor apparatus 1k according to the embodiment of the disclosure. Upon the protocol chart monitor apparatus 1k starting the monitor process, the second operation information obtaining unit 21 starts obtaining an operation information item from the robot controlling apparatus 2 (ST30). The protocol chart display unit 24 then displays the protocol chart (ST31).

After the robot 3 starts the protocol, the tracking unit 23 tracks the processing symbol corresponding to the operation being performed by the robot 3 in the protocol chart. The tracked symbol display unit 24b displays the name of the tracked processing symbol at the processing-symbol-being-executed display box 42 (ST32). The tracked symbol display unit 24b then displays the tracked symbol 47a for the tracked processing symbol (ST33).

The protocol chart monitor apparatus 1k determines whether the entire protocol has finished, based on the operation information items obtained from the robot controlling apparatus 2 (ST34). If it is determined that the protocol has not finished (NO in ST34), the tracking unit 23 continues to track the processing symbol and the protocol chart display unit 24 continues to display the protocol chart. In contrast, if it is determined that the protocol has finished (YES in ST34), the second operation information obtaining unit 21 of the protocol chart monitor apparatus 1k finishes obtaining the operation information item (ST35). The protocol chart monitor apparatus 1k then ends the monitor process.

Note that the configurations of the embodiment are described above as specific examples and that there is no intention to limit the disclosure of this specification to these specific configurations. A person skilled in the art may make various modifications, for example, alterations and additions of functions and operation methods, for the embodiment disclosed herein, and control illustrated in the flowcharts may be replaced with another control that exerts equivalent functions. It should be understood that the technical scope of the disclosure of this specification also includes such modifications.

For example, the embodiment may be implemented as first to ninth processing systems, a first monitoring method, and first and second non-transitory computer-readable recording media below.

A first processing system, at least including a processing apparatus that includes a robot configured to perform, in accordance with operation commands, processes on a container that contains an object to be processed in a biochemistry or biotechnology/life science field, includes:
an image capturing apparatus configured to continuously capture a moving image of the processes; and
a monitoring apparatus including a storage unit configured to store the moving image captured by the image capturing apparatus,
wherein the monitoring apparatus includes
a list display unit configured to display at least one of a list of the processes and a list of operation information items of the robot, and
a playback unit configured to play the moving image from a timing corresponding to a specified process or a specified operation information item.

A second processing system is the first processing system in which the playback unit plays the moving image from a time corresponding to the specified process or the specified operation information item, based on time information of the specified process or the specified operation information item.

A third processing system is the first or second processing system in which the list display unit further displays, for each of the processes, a time taken for the process or further displays, for each of the operation information items, a time taken for an operation indicated by the operation information item.

A fourth processing system is any one of first to third processing systems in which the monitoring apparatus further includes
a remaining space measuring unit configured to measure a remaining storage space of the storage unit, and
a remaining space display unit configured to display the remaining storage space.

A fifth processing system is the fourth processing system in which the monitoring apparatus further includes
a remaining space warning unit configured to issue a warning concerning the remaining storage space of the storage unit, based on the remaining storage space measured by the remaining space measuring unit, and
an abort warning unit configured to issue a warning indicating that image capturing performed by the image capturing unit has been aborted, based on the remaining storage space measured by the remaining space measuring unit.

A sixth processing system is any one of the first to fifth processing systems in which the image capturing apparatus includes
a full-view image capturing unit configured to capture a full-view moving image of the processes, and
a partial-view image capturing unit configured to capture a partial-view moving image of the process.

A seventh processing system is the sixth processing system in which the partial-view image capturing unit performs image capturing at least while the process is being performed.

An eighth processing system is any one of first to seventh processing systems further including a protocol chart monitor apparatus that includes
a protocol chart storage unit configured to store a protocol chart from which the operation commands are generated, the protocol chart at least including processing symbols indicating the processes,
a tracking unit configured to track, when the robot operates in accordance with the operation commands, the processing symbol corresponding to an operation being performed by the robot in the protocol chart, and
a protocol chart display unit configured to display the protocol chart by indicating the processing symbol tracked by the tracking unit when the robot operates in accordance with the operation commands.

A ninth processing system is the eighth processing system in which the protocol chart monitor apparatus further includes an enlarging unit configured to display a partial area of the protocol chart in an enlarged manner when the robot operates in accordance with the operation commands, and a tracked symbol display unit configured to display, when the partial area does not include the processing symbol tracked by the tracking unit, a position, in the protocol chart, of the processing symbol tracked by the tracking unit.

A first monitoring method is a method for monitoring a processing apparatus including a robot configured to perform, in accordance with operation commands, processes on a container that contains an object to be processed in a biochemistry or biotechnology/life science field, the method including:

continuously capturing a moving image of the processes;
storing the captured moving image;
displaying at least one of a list of the processes and a list of operation information items of the robot; and
playing the moving image from a timing corresponding to a specified process or a specified operation information item.

A first non-transitory computer-readable recording medium is a non-transitory computer-readable recording medium storing a computer program that causes a computer to function as the monitoring apparatus included in any one of the first to seventh processing systems.

A second non-transitory computer-readable recording medium is a non-transitory computer-readable recording medium storing a computer program that causes a computer to function as the protocol chart monitor apparatus included in the eighth or ninth processing system.

It should be understood by those skilled in the art that various modifications, combinations, sub-combinations and alterations may occur depending on design requirements and other factors insofar as they are within the scope of the appended claims or the equivalents thereof.

What is claimed is:

1. A processing system at least including a processing apparatus including a robot configured to perform, in accordance with operation commands, processes on a container that contains an object to be processed in a biochemistry, biotechnology, or life science field, the processing system comprising:

an image capturing apparatus configured to continuously capture a moving image of the processes; and a monitoring apparatus including
a storage unit configured to store the moving image captured by the image capturing apparatus,
a list display unit configured to display at least one of a list of the processes and a list of operation information items each indicating an operation of the robot, and
a playback unit configured to play the moving image from a timing corresponding to a process specified from the list of processes or an operation information item specified from the list of operation information items.

2. The processing system according to claim 1, wherein the playback unit plays the moving image from a time point corresponding to the specified process or the specified operation information item, based on time information associated with the specified process or the specified operation information item.

3. The processing system according to claim 1, wherein the list display unit further displays, for each of the processes, a time taken for the process or further displays, for each of the operation information items, a time taken for an operation indicated by the operation information item.

4. The processing system according to claim 1, wherein the monitoring apparatus further includes
a remaining space measuring unit configured to measure a remaining storage space of the storage unit, and
a remaining space display unit configured to display the remaining storage space.

5. The processing system according to claim 4, wherein the monitoring apparatus further includes
a remaining space warning unit configured to issue a warning concerning the remaining storage space of the storage unit, based on the remaining storage space measured by the remaining space measuring unit, and
an abort warning unit configured to issue a warning indicating that capturing of the moving image performed by the image capturing apparatus has been aborted, based on the remaining storage space measured by the remaining space measuring unit.

6. The processing system according to claim 1, wherein the image capturing apparatus includes
a full-view image capturing unit configured to capture a full-view moving image of a series of the processes, and
a partial-view image capturing unit configured to capture a partial-view moving image of each of the processes.

7. The processing system according to claim 6, wherein the partial-view image capturing unit captures the partial-view moving image at least while each of the processes is being performed.

8. The processing system according to claim 1, further comprising:
a protocol chart monitor apparatus including
a protocol chart storage unit configured to store a protocol chart from which the operation commands are generated, the protocol chart at least including processing symbols each indicating a corresponding one of the processes,
a tracking unit configured to track, when the robot operates in accordance with the operation commands, a processing symbol corresponding to an operation being performed by the robot from among the processing symbols in the protocol chart, and
a protocol chart display unit configured to display the protocol chart by indicating the processing symbol tracked by the tracking unit when the robot operates in accordance with the operation commands.

9. The processing system according to claim 8, wherein the protocol chart monitor apparatus further includes
an enlarging unit configured to display a partial area of the protocol chart in an enlarged manner when the robot operates in accordance with the operation commands, and
a tracked symbol display unit configured to display, when the partial area does not include the processing symbol tracked by the tracking unit, an indication of a position, in the protocol chart, of the processing symbol tracked by the tracking unit.

10. A method for monitoring a processing apparatus including a robot configured to perform, in accordance with operation commands, processes on a container that contains an object to be processed in a biochemistry, biotechnology, or life science field, the method comprising:
continuously capturing a moving image of the processes;
storing the captured moving image;
displaying at least one of a list of the processes and a list of operation information items each indicating an operation of the robot; and playing the moving image from a timing corresponding to a process specified from the list of processes or an operation information item specified from the list of operation information items.

11. A non-transitory computer-readable recording medium storing a computer program that causes a computer to perform a process of monitoring a processing apparatus including a robot configured to perform, in accordance with operation commands, processes on a container that contains an object to be processed in a biochemistry, biotechnology, or life science field, the process comprising:
continuously capturing a moving image of the processes;
storing the captured moving image;
displaying at least one of a list of the processes and a list of operation information items each indicating an operation of the robot; and
playing the moving image from a timing corresponding to a process specified from the list of processes or an operation information item specified from the list of operation information items.

12. A processing system comprising:
a processing apparatus including
a robot configured to perform, in accordance with operation commands, processes on a container that contains an object to be processed;
an image capturing apparatus configured to continuously capture a moving image of the processes; and
a monitoring apparatus including
a storage unit configured to store the moving image captured by the image capturing apparatus,
a list display unit configured to display at least one of a list of the processes and a list of operation information items each indicating an operation of the robot, and
a playback unit configured to play the moving image from a timing corresponding to a process specified from the list of processes or an operation information item specified from the list of operation information items.

* * * * *